United States Patent [19]
Wilcox et al.

[11] Patent Number: 6,150,301
[45] Date of Patent: Nov. 21, 2000

[54] CHEMICAL ABSCISSION OF FRUITS AT LOW APPLICATION RATES

[76] Inventors: Merrill Wilcox, 2911 NW. 30th Ter., Gainesville, Fla. 32605; John B. Taylor, 1420 Lemon St., DeLand, Fla. 32720

[21] Appl. No.: 09/171,887

[22] PCT Filed: Apr. 29, 1997

[86] PCT No.: PCT/US97/07684

§ 371 Date: Oct. 27, 1998

§ 102(e) Date: Oct. 27, 1998

[87] PCT Pub. No.: WO97/40681

PCT Pub. Date: Nov. 6, 1997

Related U.S. Application Data

[60] Provisional application No. 60/016,456, Apr. 29, 1996, and provisional application No. 60/028,823, Oct. 17, 1996.

[51] Int. Cl.[7] .......................... A01N 43/40; A01N 43/42; A01N 43/50; A01N 43/66; A01N 43/70

[52] U.S. Cl. .......................... 504/167; 504/168; 504/169

[58] Field of Search .................................... 504/168, 169, 504/167

[56] References Cited

U.S. PATENT DOCUMENTS

| | | | |
|---|---|---|---|
| 4,786,312 | 11/1988 | Schmierer et al. | 71/92 |
| 4,999,041 | 3/1991 | Grossmann et al. | 71/70 |
| 5,045,105 | 9/1991 | Grossmann et al. | 71/74 |
| 5,188,657 | 2/1993 | Hamprecht et al. | 504/212 |

*Primary Examiner*—S. Mark Clardy

[57] ABSTRACT

The harvesting of fruit, in particular olives and citrus fruit, is aided by inducing abscission by applying to fruit-bearing parts of the plant certain imidazolinone or sulfonylurea compounds. The compounds are applied in aqueous solution or in extremely low concentration in amounts ranging from 15 to 200 ppm, preferably from 20 to 70 ppm, by spraying to the point of incipient run-off.

42 Claims, No Drawings

CHEMICAL ABSCISSION OF FRUITS AT LOW APPLICATION RATES

This application has been filed under 35 USC 371 as the national stage of international application PCT/US97/07684, filed Apr. 29, 1997. This application claims benefit of Provisional Appl. 60/016456 filed Apr. 29, 1996 and Provisional Appl. 60/028823 filed Oct. 17, 1996.

The ability of plants to slough off organs by an active separation of cells is distinctive to higher green plants. Plant physiologists describe this process as abscission. This invention relates to the use of certain chemical compounds as agents to promote the abscission of fruits, and to compositions comprising said compounds.

The harvesting of fruit crops has traditionally been accomplished by manual labor. However, in recent years, the shortage and expense of manual labor has prompted the development of other means for picking and harvesting fruit crops. To this end, a wide variety of mechanical devices has been developed, each of which operate in accordance with a different principle in order to remove fruit from trees or plants. For example, one device utilizes giant fans for generating strong air blasts to blow the fruit from the trees. Another device includes a series of notched or toothed arms which operate by combing the tree limbs thereby raking the fruit from the trees. Finally, mechanical shakers have been developed having an arm or boom which is connected to either a branch or the trunk of the tree and operates by violently shaking the tree in order to shake the fruit loose. However, none of these devices has been entirely successful in many crops. If the fruit is firmly attached to the tree, strong air blasts or mechanical shaking cause the fruit to strike spurs, branches and other fruit thereby bruising and damaging the fruit. Since the force necessary to remove firmly-attached fruit is usually that force necessary to tear the rind, many fruits suffer open wounds and tearing when these mechanical devices, as well as the notched arms, are used. The result is poor quality fruit since there is usually a considerable time lapse between the time of harvesting and the time of final use within which the fruit is subject to decay where wounds and bruises appear. In addition, the force generated by these mechanical devices causes the removal of twigs, leaves and branches which are carried with the fruit to the processing plant. Such extraneous matter must be removed manually in order to avoid damage to the fruit processing machinery, which is a time-consuming and expensive operation. Finally, it has been observed that long periods of shaking by mechanical shakers result in bark damage and disturbance to the root system, which can easily result in long-term plant destruction.

It has now been found that by first treating the fruit-bearing plants with an appropriate chemical abscission agent, the fruits are induced to abscise with either little or no mechanical aid.

Chemicals used to assist in loosening the fruit for the harvesting operation are sometimes called, in general terms, harvesting aid chemicals or fruit loosening chemicals. If the amount of force needed to separate a fruit from the rest of the plant can be reduced through the use of chemical, this would be a significant contribution to agriculture and would be useful to farmers and growers. Such a chemical would allow pickers to pick the fruit easily and more quickly. In the case where mechanical harvesters are used, the amount of force which would have to be applied by the mechanical harvester could be reduced. More fruit per tree (per vine, or unit or row) could be harvested more easily and uniformly. Less damage to the fruit itself and to the rest of the plant would result if a chemical loosening agent effectively reduced the required harvest force. The quality of the fruit would increase because of less damage and possibly the yield per tree (per hectare, or per other unit of measure) would increase because of a more uniform and complete harvest.

This invention relates to the use of certain chemicals which have a positive and beneficial effect on the abscission process. They facilitate and make the harvesting of crops easier. To harvest fruit, whether it is done by hand or mechanically, a given amount of force (energy) must be applied by hand or mechanically to the fruit, or portion of the plant to be harvested, in order to force it to abscise, or come loose from the rest of the plant. Both manual and mechanical harvesting methods can be more commercially successful where effective abscission agents are used, since potential damage to the crop can be significantly reduced. Their use helps to keep the unit cost of production down to a reasonable level. Where hand labor is still used in harvesting crops, any practice that can help to increase the productivity of a person per unit of time would be an important agricultural contribution.

This invention is concerned with chemical compounds useful in promoting the abscission of all types of fruits. From a practical and economic standpoint, however, this invention is more concerned with the harvesting of fruit derived from fruit-bearing trees and vines having economic value, such as citrus fruits (particularly, oranges, lemons, limes and grapefruit), cherries, and olives and reference will be made to this type of fruit for illustrative purposes although it is to be understood that the invention is not intended to be limited thereby.

The precise biochemical mechanism of abscission is not of prime importance for the understanding of this invention, but the compositions disclosed herein enter into the biochemical reactions involved in the abscission cycle in a manner to induce or hasten the abscission cycle of mature or near-mature fruit. It is the purpose of this invention to disclose compositions and methods for chemically bringing about or inducing the abscission of fruit from fruit-bearing plants at the stage of fruit development just prior to full ripeness such that the fruit may be economically harvested for commercial use. Therefore, the term "abscission" as used herein refers to the separation of fruit from its tree at the stage of development at or just prior to fruit maturity.

The compounds used in the methods of this invention help to loosen the fruit which is to be harvested while, at the same time, they do not significantly damage the rest of the plant.

Various abscission agents have already been suggested, and in some cases used to a limited extent, but these are frequently unsatisfactory on account of undesirable side-effects. An example of these is cycloheximide (Cooper, U.S. Pat. No. 3,663,199) which, in spite of an excellent abscission action in the case of some citrus fruits, is not adapted to use on the "Valencia" orange, as it has a great disadvantage in that it severely damages blossoms and unripe fruit (both of which are sometimes found on the "Valencia" at harvest time), has a pronounced defoliating action, and gives rise to considerable scarring on ripe fruit. Other examples are glyoxime (Wilcox, U.S. Pat. No. 4,052,194) and 5-chloro-3-methyl-4-nitropyrazole (Crovetti, U.S. Pat. No. 3,869,274), which can also be used on "Valencia" oranges if the fruit is processed within about three days.

Although abscission agents known in the prior art have been satisfactory for some purposes, it would nevertheless be desirable to develop abscission agents which can be used on a variety of fruits and at very low application rates. The advantages in applying chemical compounds at rates lower than heretofore possible are obvious; these advantages include lower costs, less likelihood of adverse environmental effects, little or no damage to the tree, etc.

In recent years, there have been developed a number of selective herbicidal chemicals which are said to be useable at relatively low application rates. These include two broad classes of compounds which will be referred to herein as the "sulfonylureas" and the "imidazolinones". There are numerous patents disclosing a wide variety of sulfonylurea and imidazolinone compounds, including those mentioned specifically below. The inventors have found that certain specific compounds disclosed in these patents are useable as fruit abscission agents and are particularly advantageous in that they can be employed in concentrations lower than the concentrations heretofore required in abscission compositions. In general, these patents indicate that the subject compounds are useful as herbicides and some patents also describe the compounds in general terms as plant growth regulants. In some of these patents, there is a general reference to possible utility of some of the subject compounds as abscission agents, but no details are given as to specific compounds, methods of use, concentrations, crops, or any other information which would enable a person skilled in the art to use the subject compounds as abscission agents for fruit. In Willms, U.S. Pat. No. 4,440,565, there are data showing the use of tree specific sulfonylurea compounds as abscission agents for oranges, but the subject compounds are used in amounts exceeding the criteria for the useable compounds of this invention and, furthermore, the compounds disclosed in said patent are structurally distinct from the compounds useable in this invention.

This invention provides a method of aiding in the harvesting of fruit, particularly olives and citrus fruits such as oranges, lemons and grapefruit, wherein abscission is induced by application to the fruit-bearing plant an effective amount of a sulfonylurea compound or an imidazolinone compound.

The imidazolinone compounds useable in the practice of this invention are 2-[4,5-dihydro-4-methyl-4-(1-methylethyl)-5-oxo-1H-imidazol-2-yl]-arylcarboxylates of the general formula

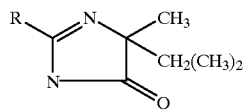

wherein R is quinolin-3-COOR$^1$, R$^2$-benzene-COOR$^1$ or 5-R$^3$-pyridine-3-COOR$^1$, in which R$^1$ is selected from the group consisting of hydrogen, methyl, ammonium and lower (i.e., C$_1$–C$_4$) alkylamine, R$^2$ is methyl in the 4- or 5-position, and R$^3$ is selected from the group consisting of hydrogen, methyl, ethyl or methoxymethyl.

The sulfonylurea compounds useable in the practice of this invention fall into two general classes, namely the N-triazinylsulfonylureas and the N-pyrimidinylsulfonylureas.

The N-triazinylsulfonylureas have the general formula

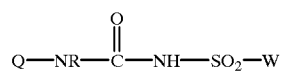

wherein R is hydrogen or methyl, Q is 4 methoxy-6-methyltriazin-2-yl or 4,6 dimethoxytriazin-2-yl and W is 2-methoxycarbonylthiophen-3, 2-(2-methoxyethoxy) phenyl, 2-(3,3,3-trifluoropropyl)phenyl, 2-(2-chloroethoxy) phenyl, 2 chlorophenyl or 2-methoxycarbonylphenyl, or wherein Q is 4 ethoxy-6-methylaminotriazin-2-yl or 4-dimethylamino-6-(2,2,2-trifluoroethoxy)triazin-2-yl and W is 2-methoxycarbonylphenyl or 2-methoxycarbonyl-6-methylphenyl.

The N-pyrimidinylsulfonylureas have the general formula

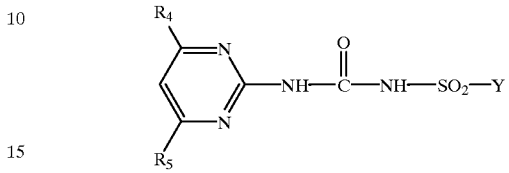

wherein R$_4$ is chloro, methyl, methoxy or difluoromethoxy, R$_5$ is methyl, methoxy or difluoromethoxy, and Y is 3-dimethylaminocarbonylpyridin-2-yl, 4-methoxycarbonyl-3-chloro-1-methyl-1H-pyrazole-5-yl, 1-methyl-4-(2-methyl-2H-tetrazol 5 yl)pyrazole-5-yl, 2-cyclopropylcarbonylphenylamino, 2-ethoxycarbonylphenyl, 2-methoxycarbonylphenyl, 2-(3-oxetanyloxy)carbonylphenyl, 2-methoxycarbonylphenylmethyl, 2-ethylsulfonylimidazo [1,2-a]pyridin-3-yl, 3-trifluoromethylpyridin 2-yl, 2-chloroimidazo[1,2-a]pyridin-3-yl or 1-methyl-4-hydroxycarbonylpyrazole 5 yl.

This invention also is directed to compositions for inducing abscission of fruit which comprises one or more of the aforementioned imidazolinone and sulfonylurea compounds. Such formulations are prepared by dissolving or mixing the active ingredient compounds with one or more carrier materials, as is well known in the formulation art.

The plants to be treated by the methods of this invention are fruit plants in general. For example, by applying appropriate compositions of this invention to citrus, olive, coffee, grape, apple, pepper, tomato, almonds, pecans, walnuts, etc., the harvest of fruits of these plants may be facilitated. Particular plants to be treated include citrus such as oranges, lemons, limes and grapefruit, and olives. Oranges, because of their economic importance, are a most particular target crop for treatment. The compounds of this invention cause fruit deterioration that is only about 5 to 12% as rapid as that caused by glyoxime (Wilcox, U.S. Pat. No. 4,052,194) or 5-chloro-3-methyl-4-nitropyrazole (Crovetti, U.S. Pat. No. 3,869,274).

Imidazolinones which are useful in the methods of this invention are disclosed in the following three U.S. patents, all of which are hereby incorporated by reference:

1. In U.S. Pat. No. 4,798,619, Example 42, columns 103–104 and preceding, is described the synthesis of 2-[4, 5-dihydro-4-methyl-4-(1-methylethyl)-5-oxo-1H-imidazol-2-yl]-3-quinolinecarboxylic acid, which has the common name imazaquin; in this same patent in Example 18, columns 79–80, are described the syntheses of 2-[4,5-dihydro-4-methyl-4-(1-methylethyl)-5-oxo-1H-imidazol-2-yl]-5-ethyl-3-pyridinecarboxylic acid, which has the common name imazethapyr, and also of ±-2-[4,5-dihydro-4-methyl-4-(1-methylethyl)-5-oxo-1H-imidazol-2-yl]-3-pyridinecarboxylic acid which has the common name imazameth; and in Example 10, columns 70–71, is described the synthesis of ±-2-[4,5-dihydro-4-methyl-4-(1-methylethyl)-5-oxo-1H-imidzaol-2-yl]-3-pyridinecarboxylic acid, which has the common name imazapyr.

2. In U.S. Pat. No. 4,188,487, columns 3–5, is described the synthesis of ±-2-[4,5-dihydro-4-methyl-4-(1-methylethyl-5-oxo-1H-imidazol-2-yl]-4(and 5)-methylbenzoic acid (3:2) which has the common name imazamethabenz; in the same patent in Example 2, columns 8–10, is described the synthesis of the methyl ester of imazamethabenz.

3. In U.S. Pat. No. 5,334,576, columns 6–9, is described the synthesis of +-5-methoxymethyl-2-[4,5-dihydro-4-methyl-4-(1-methylethyl)-5-oxo-1H-imidazol-2-yl]-3-pyridinecarboxylic acid, which has the common name imazamox.

These imidazolinones described in the above three patents are particularly effective in cool weather, and are extremely useful in the methods of this invention. The gentle, slow abscission activity at very low application rates and the very minimal damage to the released fruit in methods using these imidazolinones are particularly desirable.

Sulfonylureas which are useful in the methods of this invention are disclosed in the following 16 U.S. patents, all of which are hereby incorporated by reference:

1. In U.S. Pat. No. 4,671,819, Example H3, column 12, is described the synthesis of 1-(4-methoxy-6-methyltriazin-2yl)-3-[2-(3,3,3-trifluoropropyl)-phenylsulfonyl]-urea, which has the common name prosulfuron.

2. In U.S. Pat. No. 4,514,212, Example 2c, columns 9–10, is described the synthesis of [2-(2-chloroethoxy)-N-[(4-methoxy-6-methyl-1,3,5-triazin-2-yl)amino]carbonyl]-benzenesulfonamide, which has the common name triasulfuron; synthetic methods in this same patent may be used for the preparation of 3-(4,6-dimethoxy-1,3,5-triazin-2-yl)-1-[2-(2-methoxyethoxy)-phenylsulfonyl]urea, which has the common name cinosulfuron.

3. In U.S. Pat. No. 4,478,635, Example 2c, column 10, is described the synthesis of methyl 2-[[[[[(4,6-bis(difluoromethoxy)-2-pyrimidinyl]amino]carbonyl]amino]sulfonyl]-benzoate, which has the common name primisulfuron.

4. In U.S. Pat. No. 4,394,506, Example 3, column 21, is described the synthesis of methyl-2-[[[[(4,6-dimethyl-2-pyrimidinyl)amino]carbonyl]amino]sulfonyl]-benzoate, which has the common name sulfometuron.

5. In U.S. Pat. No. 4,547,215, Example 2, column 3, is described the synthesis of ethyl 2-[[[[(4-chloro-6-methoxy-2-pyrimidinyl)amino]carbonyl]amino]sulfonyl]-benzoate, which has the common name chlorimuron.

6. In U.S. Pat. No. 5,209,771, columns 3 and 4, is described the synthesis of 2-[[[[(4,6-dimethyl-2-pyrimidinyl)amino]carbonyl]amino]sulfonyl]-benzoic acid, 3-oxetanyl ester, which has the common name oxasulfuron.

7. In U.S. Pat. No. 4,383,113, Example 13, columns 44–45, is described the synthesis of methyl 2-[[[[(4-methoxy-6-methyl-1,3,5-triazin-2-yl)amino]carbonyl]amino]sulfonyl]-benzoate, which has the common name metsulfuron.

8. In U.S. Pat. No. 4,548,638, Example 1, column 4, is described the synthesis of methyl 2-[[[[[(4-ethoxy-6-(methylamino)-1,3,5-triazin-2-yl]amino]carbonyl]amino]sulfonyl]-benzoate, which has the common name ethametsulfuron.

9. In U.S. Pat. No. 4,740,234, Example 1, column 2, is described the synthesis of methyl 2-[[[[(4-methoxy-6-methyl-1,3,5-triazin-2 -yl)methylamino]carbonyl]amino]sulfonyl]-benzoate, which has the common name tribenuron.

10. In U.S. Pat. No. 4,789,393, Example 9, columns 11–12, is described the synthesis of 2-[[[[(4,6-dimethoxy-2-pyrimidinyl)amino]carbonyl]amino]sulfonyl]-N,N-dimethyl-3-pyridinecarboxamide, which has the common name nicosulfuron; in this same patent are methods that may be used to synthesize 1-(4,6-dimethoxypyrimidin-2-yl)-3-[3-(trifluoromethyl)-2-pyridylsulfonyl]-urea, which has the common name flazasulfuron; and also to synthesize 2-chloro-N[[(4,6-dimethoxy-2-pyrimidinyl)amino]carbonyl]imidazo(1,2-a)pyridine-3-sulfonamide, which has the common name imazosulfuron.

11. In U.S. Pat. No. 4,127,405, Example 3, column 8, is described the synthesis of 2-chloro-N-[(4-methoxy-6-methyl-1,3,5-triazin-2-yl)aminocarbonyl]-benzenesulfonamide, which has the common name chlorsulfuron.

12. In U.S. Pat. No. 4,420,325, Examples 14–16, columns 13–16, is described the synthesis of methyl 2-[[[[(4,6-dimethoxy-2-pyrimidinyl) amino]carbonyl]aminosulfonyl]methyl]-benzoate, which has the common name bensulfuron.

13. In U.S. Pat. No. 5,090,933, Example 6, column 9, is described the synthesis of methyl 2-[[[[[(4-(dimethylamino)-6-(2,2,2-trifluoroethoxy)-1,3,5-triazin-2-yl]amino]carbonyl]amino]sulfonyl]-3-methylbenzoate, which has the common name triflusulfuron.

14. In U.S. Pat. No. 5,492,884, column 2, is described the synthesis of [[[[[(4,6-dimethoxy-2-pyrimidinyl)amino]carbonyl]amino]sulfonyl]amino]-2-(cyclopropylcarbonyl)-benzene, which has the common name cyclosulfamuron.

15. in U.S. Pat. No. 4,746,353, columns 14–20, is described the synthesis of N-[[(4,6-dimethoxy-2-pyrimidinyl)-amino]carbonyl]-1-methyl-4-(2-methyl-2H-tetrazol-5-yl)]-1H-pyrazole-5-sulfonamide, which has the common name azimsulfuron.

16. In U.S. Pat. No. 4,668,277, Example 2, columns 5–6, is described the synthesis of methyl 5-[[(4,6-dimethoxy-2-pyrimidinyl)-amino carbonylaminosulfonyl]-3-chloro-1-methyl]-1-H-pyrazole-4-carboxylate, which has the common name halosulfuron; in this same patent are set forth methods that may be used to synthesize 5-(4,6-dimethyoxypyrimidin-2-ylcarbamoylsulfamoyl)-1-methylpyrazole-4-carboxylic acid, which has the common name pyrazosulfuron.

17. In U.S. Pat. No. 4,481,029, Example 34, columns 34–35, is described the synthesis of methyl 3-[[[[(4-methoxy-6-methyl-1,3,5-triazin-2-yl)amino]carbonyl]amino]sulfonyl]-2-thiophenecarboxylate, which has the common name thifensulfuron.

18. In U.S. Pat. No. 5,017,212, columns 29–40, is described the synthesis of N-(2-ethylsulfonylimidazo[1,2-a]pyridin-3-ylsulfonyl)-N'-(4,6-dimethoxy-2-pyrimidinyl)urea, which has the common name sulfosulfuron.

These sulfonylureas described in the above 16 patents are extremely useful in the methods of this invention. The gentle, slow abscission activity at very low application rates and the very minimal damage to the released fruit in methods using these imidazolinones are particularly desirable.

The active substances of this invention are not phytotoxic in the usual application concentrations, and they have low toxicity towards warm-blooded animals. Moreover, they produce no morphological changes of the plants and cause no damage to them. They promote, in particular, the development of abscission layers. Consequently, fruits of all kinds, e.g., stone fruit (e.g., cherries), berries, pomaceous fruit (e.g., apples) or oil fruits (e.g., olives), nuts, and particularly citrus fruits, can be separated from the plants, manually or mechanically, without any great amount of force being applied. Damage to foliage, branches, or fruit, which normally occurs when fruit is removed by the shaking of trees and shrubs, or by the plucking of the fruit from the branches, is largely avoided, and the production capacity of the trees is thus increased.

The extent and nature of the action are governed by the most diverse factors, depending on the type of plant, and particularly on the applied concentration and on the time of application with regard to the stage of development of the plant and the fruit. Thus, for example, plants of which the fruits is to be sold, or in some other way utilized, are treated immediately after blossoming or at an appropriate length of time before the gathering of the fruit. The active substances are applied preferably in the form of liquid preparations, these being applied to parts of plants above the soil, to the surface of the soil or into the soil. Application to parts of plants above the soil is preferred, for which purpose solutions or aqueous dispersions are most suitable.

The active substances of this invention may be used together with suitable carriers, solvents and/or other additives, or in many cases as formulated by the manufacturer. A preferred adjuvant is Silwet L-77, a non-ionic adjuvant, a silicon-polyether copolymer distributed by Loveland Industries, Inc., but one skilled in the art can substitute other adjuvants with acceptable results. Suitable carriers and additives can be solid or liquid, and correspond to the substances normally used in formulation practice, for example, solvents, diluents, dispersing agents, wetting agents, other surfactants, adhesives and thickening or bonding agents. Most conveniently, the formulations will be prepared in concentrated form to which water can be added to produce the solutions and slurries described above. As used herein, the term "carrier" refers to all of the solvents diluents, surfactants, etc., comprising the subject formulations, other than the active imidazolinone or sulfonylurea ingredient.

The applied amounts are largely governed by the purpose and nature of the application (treatment of the soil or of parts of plants). The usual concentrations applied to above-ground parts of fruit crops are between about 15 ppm and about 200 ppm, in aqueous solution or slurry, to incipient run-off. It is preferable, for environmental and other reasons, to use the subject compounds in as low concentrations as possible. Therefore, it is preferable to employ concentrations below 100 ppm if possible and more preferable to employ concentrations below 60 ppm. These application rates are unusually low, and therefore environmentally desirable as they produce less burden of extraneous compounds in the environment. It has been found that suitable application rates for the sulfonylureas are from 20 to 50 ppm, with a rate of about 30 ppm being especially preferred. For the imidazolinones, the preferred rates are somewhat higher, namely in the range of 40 to 70 ppm, with a rate of about 50 ppm being especially preferred. The optimum time of application to promote fruit abscission is shortly before harvesting, i.e., about 3 days to 4 weeks before harvesting. In typical orange groves, the aqueous solution or slurry is applied at a rate of about 46 to 460 liters per hectare (30–300 gallons per acre).

EXAMPLES

In the following examples, abscission agents are applied at low pressure to the point of incipient run-off to branches carrying a counted number of fruit or to whole fruit trees. Concentrations are expressed in parts of active ingredient per million parts of carrier (ppm). Silwet L-77 was added to carrier and control water at 2 ml per gallon (3.8 liters). Other adjuvants used in addition in some examples were foliar fertilizers: urea; triazone, $N/P_2O_5/K_2O=28-0-0$ and KP3, potassium phosphonate, $N/P_2O_5K_2O=0-22-20$. At a specified number of days after treatment (DAT), the pull force (PF) (in lb) needed to remove the fruit as measured by means of a Hunter Force Gauge is recorded. Fallen mature fruit is recorded as 0 lb (0 Kg), or in some cases recorded as % MFD (% Mature Fruit Drop). Fruit that is too loose to deflect the Hunter Force Gauge is recorded as 0 lb (0 Kg), or in some cases recorded as % TLP (% Too Loose to Pull). Young fruit drop is recorded as % YFD and leaf drop as % LD where either is present. Cultivars where completely known are reported as "Scion/stock", as in "Valencia/sour orange", or otherwise where only the scion is known "Valencia".

Example 1

Sulfometuron and three other compounds are applied to "Valencia/sour orange" cultivar in a replicated branch test to determine citrus abscission activity. All materials are applied at 30 ppm to 10 fruit per branch in each of three replicates at an ambient temperature of 16° C. (60° F.) in Orange County, Florida. Pull force determinations are made 21 days after application.

| Treatment | Rate Applied, ppm | Pull Force | |
|---|---|---|---|
| | | lb. | Kg. |
| Sulfometuron | 30 | 0 | 0 |
| Triasulfuron | 30 | 4.2 | 1.9 |
| Nicosulfuron | 30 | 6.0 | 2.7 |
| Primisulfuron | 30 | 3.0 | 1.4 |
| Control | — | 19.1 | 8.7 |

Example 2

Abscission treatments are applied to three replications of five fruit on one branch of "Hamlin/sour orange". Pull forces are measured 15 days after treatment.

| Treatment | Rate Applied, ppm | Pull Force | |
|---|---|---|---|
| | | lb. | Kg. |
| Sulfometuron | 30 | 1.0 | 0.5 |
| Sulfometuron | 90 | 0. | 0 |
| Glyoxime | 600 | 4.5 | 2.0 |
| Control | — | 16.5 | 7.5 |

Example 3

Sulfometuron and hexazinone are compared at 30 and 90 ppm. All treatments are applied to three branches of 10 fruit each assigned in completely randomized design to "Valencia" oranges. Results are noted two weeks after treatment.

| Treatment | Rate Applied, ppm | % MFD | % YFD |
|---|---|---|---|
| Sulfometuron | 30 | 74.2 | 0 |
| Sulfometuron | 90 | 84.6 | 0 |
| Hexazinone | 30 | 0 | 0 |
| Hexazinone | 90 | 0 | 10 |
| Control | — | 0 | 0 |

Example 4

Sulfometuron at 90 ppm is compared to glyoxime at 600 ppm on "Hamlin" oranges at an ambient temperature of 11°

C. (52° F.). Single branches of 10 fruit each are used in each of three replications in a completely randomized design. Results are noted 15 days after treatment.

| | | Pull Force | |
|---|---|---|---|
| Treatment | Rate Applied, ppm | lb. | Kg. |
| Sulfometuron | 90 | 1.6 | 0.7 |
| Glyoxime | 600 | 7.3 | 3.3 |
| Control | — | 18.1 | 8.2 |

Example 5

Sulfometuron, metsulfuron, and chlorsulfuron, all at 30 ppm, are compared to phosphorous acid, hypophosphorous acid, dibutylurea, and glyoxime, all at 600 ppm on "Hamlin" oranges. Pull force for fruit removal is measured after three weeks as an average of three replicated branches (five fruit) assigned in a completely randomized design.

| | | Pull Force | |
|---|---|---|---|
| Treatment | Rate Applied, ppm | lb. | Kg. |
| Sulfometuron | 30 | 1.9 | 0.9 |
| Metsulfuron | 30 | 7.2 | 3.3 |
| Chlorsulfuron | 30 | 7.4 | 3.4 |
| Hypophosphorous acid | 600 | 17.1 | 7.7 |
| Phosphorous acid | 600 | 16.6 | 7.5 |
| Dibutylurea | 600 | 12.7 | 5.8 |
| Glyoxime | 600 | 3.3 | 1.5 |
| Control | — | 17.8 | 8.1 |

Example 6

Abscission treatments are applied to a single four-year-old whole trees of "Parson Brown/Carizzo". Pull forces and other data are recorded on 10 oranges per tree eight days after treatment.

| | | | | Pull Force | |
|---|---|---|---|---|---|
| Treatment | Rate Applied, ppm | % MFD | % LD | lb. | Kg. |
| Imazameth | 90 | 0 | 0.5 | 11.2 | 5.1 |
| Imazameth + 2% KP3 | 90 | 65 | 1.0 | 2.6 | 1.2 |
| 2% KP3 | | 0 | 1.0 | 18.1 | 8.2 |
| Control | — | 0 | 0.5 | 20.2 | 9.2 |

Example 7

Abscission treatments are applied to single four-year-old trees of "Parson Brown/Carizzo". Pull forces and other data are recorded on 10 oranges per tree 14 days after treatment.

| | | | | Pull Force | |
|---|---|---|---|---|---|
| Treatment | Rate Applied, ppm | % MFD | % LD | lb. | Kg. |
| Imazameth | 90 | 87 | 1.0 | 0 | 0 |

-continued

| | | | | Pull Force | |
|---|---|---|---|---|---|
| Treatment | Rate Applied, ppm | % MFD | % LD | lb. | Kg. |
| Imazameth | 90 | | | | |
| + 2% KP3 | | 94 | 1.0 | 0 | 0 |
| 2% KP3 | | 0 | 1.0 | 19.6 | 8.9 |
| Control | — | 0 | 0.5 | 21.0 | 9.5 |

Example 8

Abscission treatments are applied to single four-year-old whole trees of "Parson Brown/Carizzo". Pull forces and other data are recorded on 10 oranges per tree nine days after treatment.

| | | | | Pull Force | |
|---|---|---|---|---|---|
| Treatment | Rate Applied, ppm | % MFD | % LD | lb. | Kg. |
| Sulfometuron | 30 | 65 | 0.5 | 4.2 | 1.9 |
| Sulfometuron | 30 | | | | |
| + 2% KP3 | | 90 | 1.0 | 0 | 0 |
| 2% KP3 | | 0 | 1.0 | 19.6 | 8.9 |
| Control | — | 0 | 0.5 | 21.0 | 9.5 |

Example 9

Abscission treatments are applied to single four-year-old whole trees of "Parson Brown/Carizzo". Pull forces and other data are recorded on 10 oranges per tree 15 days after treatment.

| | | | | Pull Force | |
|---|---|---|---|---|---|
| Treatment | Rate Applied, ppm | % MFD | % LD | lb. | Kg. |
| Sulfometuron | 23 | 72.0 | 0.5 | 4.6 | 2.1 |
| Sulfometuron | 23 | | | | |
| + 2% KP3 | | 86.0 | 0.5 | 0 | 0 |
| 2% KP3 | | 0 | 0.5 | 20.9 | 9.5 |
| Control | — | 0 | 0.5 | 19.6 | 8.9 |

Example 10

Abscission treatments are applied to single four-year-old whole trees of "Parson Brown/Carizzo". Pull forces and other data are recorded on 10 oranges per tree 19 days after treatment.

| | | | | Pull Force | |
|---|---|---|---|---|---|
| Treatment | Rate Applied, ppm | % MFD | % LD | lb. | Kg. |
| Sulfometuron | 23 | 85 | 0 | — | — |
| Sulfometuron + 2% Triazone | 23 | 95 | 0.5 | — | — |
| Imazameth | 60 | | | | |
| Imazameth + 2% Triazone | 60 | 95 | 0 | — | — |
| Control | — | 0 | 0 | 20.6 | 9.4 |

Example 11

Abscission treatments are applied to single four-year-old whole trees of "Parson Brown/Carizzo". Pull forces and other data are recorded on 10 oranges per tree 13 days after treatment.

| Treatment | Rate Applied, ppm | % MFD | % LD | Pull Force lb. | Kg. |
|---|---|---|---|---|---|
| Imazameth | 70 | 50 | 0 | — | — |
| Imazameth + 2% Urea | 70 | 75 | 0.5 | — | — |
| Sulfometuron | 23 | 30 | 0.5 | — | — |
| Sulfometuron + 2% Urea | 23 | 95 | 10 | — | — |
| Control | — | 0 | 0 | 19.8 | 9.0 |

Example 12

Abscission treatments are applied to single whole trees of "Hamlin/Carizzo" on January 3. Temperatures fall to about −4° C. (mid-20° F.) on January 7, 8 and 9. Pull forces and other data are recorded 21 days after treatment on January 24.

| Treatment | Rate Applied, ppm | % MFD | % LD | Pull Force lb. | Kg. |
|---|---|---|---|---|---|
| Prosulfuron | 30 | 55 | 1 | — | — |
| Prosulfuron + Triasulfuron | 15 / 15 | 65 | 2 | — | — |
| Primisulfuron | 30 | 40 | 2 | — | — |
| Oxasulfuron | 30 | 55 | 2 | — | — |
| Control | — | 0 | 2 | 15.6 | 7.1 |

Example 13

Abscission treatments are applied to single four-year-old whole trees of "Parson Brown/Carizzo". Pull forces and other data are recorded on 10 oranges per tree 15 days after treatment.

| Treatment | Rate Applied, ppm | % MFD | % LD | Pull Force lb. | Kg. |
|---|---|---|---|---|---|
| Prosulfuron | 30 | 80 | 0 | — | — |
| Triasulfuron | 30 | 90 | 1 | — | — |
| Primisulfuron | 30 | 40 | 0 | — | — |
| Oxasulfuron | 30 | 95 | 0 | — | — |
| Control | — | 0 | 0 | 19.4 | 8.8 |

Example 14

Abscission treatments are applied to single four-year-old whole trees of "Parson Brown/Carizzo". Pull forces and other data are recorded on 10 oranges per tree 13 days after treatment.

| Treatment | Rate Applied, ppm | % MFD | % LD | Pull Force lb. | Kg. |
|---|---|---|---|---|---|
| Imazameth | 70 | 80 | 0 | — | — |
| Imazameth + 1% Triazone | 70 | 90 | 0 | — | — |
| Control | — | 0 | 0 | 20.4 | 9.3 |

Example 15

Abscission treatments are applied to four branches (i.e., four replications) of "Hamlin" orange. Pull forces and other data are recorded on 10 oranges per replication 21 days after treatment.

| Treatment | Rate Applied, ppm | Pull Force lb. | Kg. |
|---|---|---|---|
| Imazapyr | 45 | 8.1 | 3.7 |
| Imazameth | 45 | 4.5 | 2.0 |
| Imazethapyr | 45 | 7.3 | 3.3 |
| Control | — | 12.5 | 5.7 |

Example 16

Abscission treatments are applied to four branches (i.e., four replications) of "Hamlin" orange. Pull forces are recorded on 10 oranges per replication 21 days after treatment.

| Treatment | Rate Applied, ppm | Pull Force lb. | Kg. |
|---|---|---|---|
| Imazaquin | 135 | 4.3 | 2.0 |
| Imazapyr | 135 | 1.1 | 0.5 |
| Imazethapyr | 135 | 0.2 | 0.1 |
| Sulfometuron | 90 | 1.0 | 0.5 |
| Control | — | 17.1 | 7.7 |

Example 17

Abscission treatments are applied to four branches (i.e., four replications) of "Hamlin" orange. Pull forces are recorded on 10 oranges per replication 15 days after treatment.

| Treatment | Rate Applied, ppm | Pull Force lb. | Kg. |
|---|---|---|---|
| Imazapyr | 135 | 3.3 | 1.5 |
| Imazameth | 45 | 0.8 | 0.4 |
| Imazameth | 90 | 0.0 | 0.0 |
| Imazameth | 135 | 0.2 | 0.1 |
| Glyoxime | 600 | 2.5 | 1.1 |
| Control | — | 16.6 | 7.5 |

Example 18

Abscission treatments are applied to three branches (i.e., three replications) of "Valencia" orange. Pull forces are recorded on 10 oranges per replication 30 days after treatment.

| Treatment | Rate Applied, ppm | Pull Force | |
|---|---|---|---|
| | | lb. | Kg. |
| Imazameth | 45 | 4.3 | 2.0 |
| Imazameth | 60 | 1.4 | 0.6 |
| Imazameth | 90 | 0.0 | 0.1 |
| Imazameth | 135 | 1.1 | 0.5 |
| Sulfometuron | 90 | 1.5 | 0.7 |
| Control | — | 22.7 | 10.3 |

Example 19

Abscission treatments are applied to three branches (i.e., three replications) of "Hamlin" orange. Pull forces are recorded on 10 oranges per replication 21 days after treatment.

| Treatment | Rate Applied, ppm | Pull Force | |
|---|---|---|---|
| | | lb. | Kg. |
| Imazameth | 60 | 2.1 | 1.0 |
| Sulfometuron | 30 | 1.7 | 0.8 |
| Phosphorous Acid | 600 | 17.8 | 8.1 |
| Dibutylurea | 600 | 16.9 | 7.7 |
| Glyoxime | 600 | 18.1 | 8.2 |
| Control | — | 19.2 | 8.7 |

Example 20

Abscission treatments are applied to four branches (i.e., four replications) of "Valencia" orange. Pull forces are recorded on 10 oranges per replication 14 days after treatment.

| Treatment | Rate Applied, ppm | Pull Force | |
|---|---|---|---|
| | | lb. | Kg. |
| Imazapyr | 90 | 1.5 | 0.7 |
| Imazameth | 90 | 1.4 | 0.6 |
| Imazethapyr | 90 | 6.1 | 2.8 |
| Imazaquin | 90 | 6.0 | 2.7 |
| Imazamox | 90 | 6.6 | 3.0 |
| Imazamethabenz | 90 | 7.7 | 3.5 |
| Control | — | 23.8 | 10.9 |

Example 21

Abscission treatments are applied to single whole trees of "Hamlin/Carizzo" on January 3. Temperatures fall to about −4° C. (mid-20° F.) on January 1, 8 and 9. Pull forces and other data are recorded from 10 fruit 21 days after treatment on January 24.

| Treatment | Rate Applied, ppm | % MFD | % LD | Pull Force | |
|---|---|---|---|---|---|
| | | | | lb. | Kg. |
| Prosulfuron | 15 | | | | |
| + Triasulfuron | 15 | 65 | 2 | — | — |
| Primisulfuron | 30 | 40 | 2 | — | — |
| Oxasulfuron | 30 | 55 | 2 | — | — |
| Control | — | 0 | 2 | 15.6 | 7.1 |

Example 22

Abscission treatments are applied to single whole trees of "Hamlin/Carizzo". Pull forces and other data are recorded from 10 fruit seven DAT and 14 DAT.

| | | 7 DAT | | | 14 DAT | | |
|---|---|---|---|---|---|---|---|
| Treatment | Rate Applied, ppm | % MFD | % LD | PF | % MFD | % LD | LF |
| Prosulfuron | 30 | 10 | 2 | | 80 | 2 | |
| Triasulfuron | 30 | 55 | 2 | | 90 | 2 | |
| Primisulfuron | 30 | 80 | 2 | | 95 | 2 | |
| Oxasulfuron | 30 | 65 | 2 | | 90 | 2 | |
| Control | — | 0 | 2 | 15.6 | | | 14.0 |

Example 23

Abscission treatments are applied to single whole trees of "Parson Brown/Cleo" on January 3. Temperatures fall to about −4° C. (mid-20° F.) on January 1, 8 and 9. Pull forces and other data are recorded from 10 fruit 21 days after treatment on January 24.

|  |  |  |  | Pull Force | |
| --- | --- | --- | --- | --- | --- |
| Treatment | Rate Applied, ppm | % MFD | % LD | lb. | Kg. |
| Prosulfuron | 30 | 55 | 1 | — | — |
| Prosulfuron + 1% KP3 | 30 | 65 | 1 | — | — |
| 1% KP3 |  | 0 | 2 | 15.0 | 6.8 |
| Control | — | 0 | 1 | 17.2 | 7.8 |

Example 24

Abscission treatments are applied to three branches (i.e., three replications) of "Hamlin" orange. Observations are recorded on 10 oranges per replication 21 days after treatment.

|  |  |  | Pull Force | |
| --- | --- | --- | --- | --- |
| Treatment | Rate Applied, ppm | % MFD | lb. | Kg. |
| Halosulfuron | 31 | 0 | 11.5 | 5.2 |
| Chlorsulfuron | 31 | 50 | — | — |
| Tribenuron | 31 | 55 | — | — |
| Metsulfuron | 31 | 60 | — | — |
| Sulfometuron | 31 | 65 | — | — |
| Imazaquin | 64 | 55 | — | — |
| Imazethapyr | 64 | 55 | — | — |
| Control | — | 0 | 12.5 | 5.7 |

Example 25

Applying the following abscission treatments as described in Example 24 should result in the great majority of treated fruit being too loose to pull 21 days after treatment, with untreated fruit tightly adherent.

| Treatment | Rate Applied, ppm |
| --- | --- |
| Triflusulfuron | 30 |
| Ethametsulfuron | 30 |
| Azimsulfuron | 30 |
| Bensulfuron | 30 |
| Cyclosulfamuron | 30 |

Example 26

Applying the following abscission treatments to olives or pecans, otherwise as described in Example 24 should result in the great majority of treated fruit falling to the ground within 21 days after treatment, with untreated fruit tightly adherent.

| Treatment | Rate Applied, ppm |
| --- | --- |
| Prosulfuron | 40 |
| Triasulfuron | 40 |
| Primisulfuron | 40 |
| Oxasulfuron | 40 |
| Sulfometuron | 40 |
| Imazameth | 80 |
| Imazapyr | 80 |

Example 27

Applying the following abscission treatments as described in Example 24 should result in the great majority of treated fruit being too loose to pull 21 days after treatment, with untreated fruit tightly adherent.

| Treatment | Rate Applied, ppm |
| --- | --- |
| Cinosulfuron | 30 |
| Imazosulfuron | 30 |
| Pyrazosulfuron | 30 |
| Sulfosulfuron | 30 |
| Flazasulfuron | 50 |
| Imazamox | 50 |
| Cyclosulfamuron | 30 |

Example 28

Commercially formulated prosulfuron of 57% concentration is diluted to 30 ppm in water containing 2 ml Silwet per gallon (3.8 liters), and the resultant solution applied to the point of incipient run-off to entire mature "Valencia/sour orange" trees. Ten days later, 95% of the fruit have pull force of less than 4 lbs. (1.8 kg.). Twenty-one days after treatment, 97% of the fruit are on the ground. Forty days after treatment, the fallen fruit are still in good condition on the ground.

We claim:

1. A method of aiding in the harvesting of fruit which comprises inducing abscission of said fruit by applying to a fruit-bearing plant an effective amount of a 2-[4,5-dihydro-4-methyl-4-(1-methylethyl)-5-oxo-1H-imidazol-2-yl]-arylcarboxylate compound of the formula

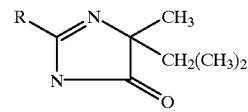

wherein R is quinolin-3-$COOR_1$, $R_2$-benzene-$COOR_1$ or 5-$R_3$-pyridine-3-$COOR_1$, in which $R_1$ is selected from the group consisting of hydrogen, methyl, ammonium and $C_1$–$C_4$ alkylamine, $R_2$ is methyl in the 4- or 5-position, and $R_3$ is selected from the group consisting of hydrogen, methyl, ethyl or methoxymethyl.

2. A method according to claim 1 in which the compound is dissolved or dispersed in water at a concentration of from about 15 to about 200 ppm and the aqueous solution or slurry is applied to the fruit-bearing areas of the plant to the point of incipient run-off.

3. A method according to claim 2 in which the compound is dissolved or dispersed in water at a concentration of from 40 to 70 ppm.

4. A method according to claim 3 in which the compound is dissolved or dispersed in water at a concentration of about 50 ppm.

5. A method according to claim 3 in which the compound is imazaquin or a salt thereof.

6. A method according to claim 3 in which the compound is imazethapyr or a salt thereof.

7. A method according to claim 4 in which the compound is imazapyr or a salt thereof.

8. A method according to claim 4 in which the compound is imazameth or a salt thereof.

9. A method according to claim 2 in which the compound is imazamox or a salt thereof.

10. A method according to claim 2 in which the compound is imazamethabenz or a slat or the methyl ester thereof.

11. The method of claim 2 in which the fruit is olives or a citrus fruit.

12. The method of claim 11 in which the fruit is a citrus fruit.

13. A method of aiding in the harvesting of fruit which comprises inducing abscission of said fruit by applying to the fruit-bearing plant an effective amount of a sulfonylurea compound of the formula

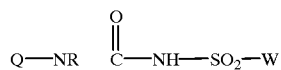

wherein Q is 4-methoxy-6-methyltriazin-2-yl or 4,6 dimethoxytriazin-2 yl, R is hydrogen or methyl and W is 2-methoxycarbonylthiophen-3, 2-(2 methoxyethoxy) phenyl, 2-(3,3,3-trifluoropropyl)phenyl, 2-(2-chloroethoxy) phenyl, 2-chlorophenyl or 2-methoxycarbonylphenyl, or wherein Q is 4-ethoxy-6-methylaminotriazin-2-yl or 4-dimethyl amino-6 (2,2,2-trifluoroethoxy)triazin-2-yl, R is hydrogen and W is 2-methoxycarbonylphenyl or 2-methoxycarbonyl-6-methylphenyl.

14. A method according to claim 13 in which the compound is dissolved or dispersed in water at a concentration of from about 15 to about 200 ppm and the aqueous solution or slurry is applied to the fruit-bearing areas of the plant to the point of incipient run-off.

15. A method according to claim 14 in which the compound is dissolved or dispersed in water at a concentration of from 20 to 50 ppm.

16. A method according to claim 15 in which the compound is dissolved or dispersed in water at a concentration of about 30 ppm.

17. A method according to claim 15 in which the compound is prosulfuron.

18. A method according to claim 15 in which the compound is triasulfuron.

19. A method according to claim 13 in which the compound is metsulfuron.

20. A method according to claim 14 in which the compound is chlorsulfuron.

21. A method according to claim 14 in which the compound is tribenuron.

22. A method according to claim 14 in which the compound is triflusulfuron.

23. A method according to claim 14 in which the compound is ethametsulfuron.

24. A method according to claim 15 in which the compound is thifensulfuron.

25. The method of claim 14 in which the fruit is olives or a citrus fruit.

26. The method of claim 25 in which the fruit is a citrus fruit.

27. A method of aiding in the harvesting of fruit which comprises inducing abscission of said fruit by applying to the fruit-bearing plant an effective amount of a sulfonylurea compound of the formula

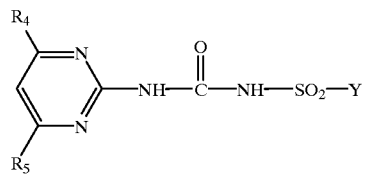

wherein $R_4$ is chloro, methyl, methoxy or difluoromethoxy, $R_5$ is methyl, methoxy or difluoromethoxy, and Y is 3-dimethylaminocarbonylpyridin-2-yl, 4-methoxycarbonyl-3-chloro-1-methyl-1H-pyrazole-5-yl, 1 methyl-4-(2-methyl-2H-tetrazol-5-yl)-pyrazole-5-yl, 2-cyclopropylcarbonylphenylamino, 2-ethoxycarbonylphenyl, 2-methoxy-carbonylphenyl, 2-(3-oxetanyloxy)carbonylphenyl, 2-methoxycarbonylphenylmethyl, 2-ethylsulfonylimidazo[1,2-a]pyridin-3-yl, 3-trifluoromethylpyridin-2-yl, 2-chloroimidazo[1,2-a]pyridin 3-yl or 1-methyl-4-hydroxycarbonylpyrazole-5-yl.

28. A method according to claim 27 in which the compound is dissolved or dispersed in water at a concentration of from about 15 to about 200 ppm and the aqueous solution or slurry is applied to the fruit-bearing areas of the plant to the point of incipient run-off.

29. A method according to claim 28 in which the compound is dissolved or dispersed in water of a concentration of from 20 to 50 ppm.

30. A method according to claim 29 in which the compound is dissolved or dispersed in water at a concentration of about 30 ppm.

31. A method according to claim 28 in which the compound is nicosulfuron.

32. A method according to claim 28 in which the compound is azimsulfuron.

33. A method according to claim 28 in which the compound is primisulfuron.

34. A method according to claim 28 in which the compound is sulfometuron.

35. A method according to claim 28 in which the compound is oxasulfuron.

36. A method according to claim 28 in which the compound is chlorimuron.

37. A method according to claim 27 in which the compound is bensulfuron.

38. A method according to claim 28 in which the compound is cyclosulfamuron.

39. A method according to claim 28 in which the compound is sulfosulfuron.

40. A method according to claim 27 in which the compound is halosulfuron.

41. The method of claim 28 in which the fruit is olives or a citrus fruit.

42. The method of claim 41 in which the fruit is a citrus fruit.

* * * * *